United States Patent [19]

Nussbaum et al.

[11] 4,177,207
[45] * Dec. 4, 1979

[54] PETROLEUM SULFONATES

[75] Inventors: Marvin L. Nussbaum, Skokie; Edward A. Knaggs, Deerfield, both of Ill.

[73] Assignee: Stepan Chemical Company, Northfield, Ill.

[*] Notice: The portion of the term of this patent subsequent to Apr. 10, 1996, has been disclaimed.

[21] Appl. No.: 883,128

[22] Filed: Mar. 3, 1978

Related U.S. Application Data

[63] Continuation-in-part of Ser. No. 676,470, Apr. 13, 1976, Pat. No. 4,148,821, which is a continuation-in-part of Ser. No. 515,013, Oct. 16, 1974, abandoned, which is a continuation-in-part of Ser. No. 432,439, Jan. 11, 1974, abandoned, which is a continuation-in-part of Ser. No. 9,065, Feb. 5, 1970, abandoned.

[51] Int. Cl.$^2$ .................. C07C 139/00; C09K 3/00
[52] U.S. Cl. ...................... 260/504 R; 260/505 R; 252/8.55 D
[58] Field of Search ............ 260/513 T, 505 E, 505 S, 260/505 R, 504 R

[56] References Cited

U.S. PATENT DOCUMENTS 3,887,611   6/1975   Sweeney .................. 260/513 T

Primary Examiner—Alan Siegel

[57] ABSTRACT

Petroleum sulfonates yielding improved results in enhanced oil recovery processes are comprised of a reaction product obtained from a mixture of a major proportion of a petroleum oil feed stock, such as a crude or a portion thereof, and a minor proportion of an additive, such as an oxygenated hydrocarbon, i.e., an oxo-alcohol or the like, reacted with $SO_3$ under sulfonation conditions, mixed with about 0.5 to 20% (by reaction mixture weight) of water at the temperature in the range of about 50° to 150° C. for a relatively brief period of time and then neutralizing the resultant material with an base, such as NaOH. The neutralized petroleum sulfonated material thus obtained, which may or may not be extracted to remove unsulfonated organic material or salts, is then formulated into a slug for injection into an oil field for enhanced oil recovery.

50 Claims, No Drawings

PETROLEUM SULFONATES

CROSS-REFERENCE TO RELATED APPLICATIONS

This is a continuation-in-part application of our U.S. Ser. No. 676,470, filed Apr. 13, 1976 (now U.S. Pat. No. 4,148,821), which in turn is a continuation-in-part of our U.S. Pat. Ser. No. 515,013, filed Oct. 16, 1974 (now abandoned), which in turn is a continuation-in-part of our U.S. Ser. No. 432,439, filed Jan. 11, 1974 (now abandoned), which in turn is a continuation-in-part of our U.S. Ser. No. 9,065, filed Feb. 5, 1970 (now abandoned), all of which are incorporated herein by reference.

BACKGROUND OF THE INVENTION

1. Field of the Invention

The invention relates to enhanced oil recovery and somewhat more particularly to improved petroleum sulfonate products useful in enhanced oil recovery and a method of producing and utilizing such sulfonate products.

2. Prior Art

The petroleum industry has recognized for many years that only a small fraction of the original petroleum (i.e., crude oil) within a given reservoir is expelled by natural mechanisms. Further, it is recognized that conventional methods of supplementing natural recovery are relatively inefficient and economically unattractive. Typically, a reservoir may retain as much as half to two-thirds of the original petroleum therein, even after the application of currently available secondary recovery techniques, such as waterflooding. Conventionally, waterflooding involves injecting at least water, through one or more input wells to drive petroleum from the reservoir formation to a geometrically offset production well. Further improvements in oil recovery can be attained with certain enhanced oil recovery techniques, wherein oil recovery systems are formulated into micellar systems with surface-active agents, injected into input wells and driven or pushed through the reservoir formation to provide additional amounts of petroleum.

Surface-active agents or surfactants typically utilized for improving the efficiency of enhanced petroleum recovery methods must no only be economical but must also be compatible with the reservoir environment. Typically, such an environment includes localized higher temperatures, higher salt and/or polyvalent ion concentrations, adsorptive petroleum-bearing or petroleum-loving surfaces, minute pore spaces, etc., all of which potentially affect the surfactant and the petroleum recovery obtained by the use of such a surfactant. For example, petroleum retained within a reservoir after natural and/or secondary recovery processes are terminated, may be in the form of discontinuous globules or discrete droplets which are trapped within the pore spaces of the reservoir, along with connate, brackish or the like water at some particular temperature. Because of the normal interfacial tension between the reservoir petroleum and water in high, such discrete petroleum droplets are unable to sufficiently deform to pass through the narrow constrictions of the individual pore channels. Similarly, reservoir petroleum appears to have a greater affinity to the petroleum-bearing surfaces, i.e., rocks, sand, etc. than does the water so that any applied force merely pushes the water to an area of less pressure, i.e., a production well, while leaving the petroleum in place on the reservoir surfaces. When surface-active agents are formulated into an oil recovery system and injected into a reservoir, they function in numerous ways, one of which is to lower the interfacial tension between the flowable materials within a reservoir and permit the petroleum droplets to deform and flow with the surfactants in the flood water system toward a production well. It is generally conceded that the interfacial tension between the flood water system and the reservoir petroleum must be reduced to an order or less than about 0.1 dynes/cm for effective recovery. Surface-active agents must also be stable in the presence of higher temperatures encountered in at least some reservoirs and be stable in the presence of highly brackish water or polyvalent ions present in certain reservoirs and yet be able to "wash" the reservoir surfaces so as to release all or almost all petroleum adsorbed therein so as to achieve an economical and effective recovery process.

One of the more promising surface-active agents used in enhanced oil recovery are the petroleum sulfonates. Generally, these agents comprise the reaction products of a petroleum feed stock and a select material yielding a sulfo radical to the petroleum feed stock, i.e., oleum or gaseous or liquid $SO_3$. Depending on many variables, such as the nature of the initial petroleum feed stock, the nature of the sulfo radical yielding material, the sulfonation reaction conditions selected, etc., the resulting petroleum sulfonates may be formulated with a wide variety of properties making them useful in enhanced oil recovery processes as well as in other fields of use, such as industrial surfactants, as blending agents for lubricating oils, as agricultural emulsifiers, dispersants, etc. However, economic and efficient production of petroleum sulfonates is difficult and the art is replete with various suggestions for achieving a more or less universally acceptable reaction process, even though most, if not all of the prior art processes leave much to be desired in terms of product control, economic availability of feed stocks, field of optimum surface-active properties, etc. In our earlier referenced disclosures, we teach a method of sulfonating petroleum oil feed stocks which provides a high yield of petroleum sulfonates and a method for formulating such sulfonates into enhanced oil recovery systems.

As a continuous part of our work in this field, we have conducted numerous core flood experiments on various crudes with various "slugs" containing various petroleum sulfonates in an effort to obtain optimum petroleum recovery under various reservoir conditions. As a part of these studies, we noticed that certain petroleum sulfonates tend to yield good petroleum recovery at certain conditions but yield different results at other conditions. We undertook to investigate the reason for such divergent results.

In enhanced oil recovery processes, the economics of a select recovery process and/or a surface-active agent, such as a petroleum sulfonate, are extremely stringent. Suggestions have been made in the art, that in order to minimize shipping and production costs, to either produce the petroleum sulfonate in-situ, as by injecting select reactive material directly into a reservoir, allowing a reaction to take place therein and then flooding the resulting reservoir with a water system to intermix with whatever reaction products are formed therein or to produce the petroleum sulfonates at the reservoir site and then formulate the resultant reaction product into a desired slug composition and inject such slug into the reservoir. However, neither of these suggestions have proven satisfactory since with the first suggestion, no control of reaction conditions or reaction products is available and with the second, insufficient quality control results, particularly since initial feed stocks, reaction conditions, etc. may vary from site to site. Further, the reaction products obtained from a typical petroleum sulfonation reaction tend to be non-homogeneous and unstable over a period of time so that the properties of such products vary. Typically, a petroleum sulfonation acidic reaction product mixture tends to separate into at least two phases, comprised of sulfonated sulfonatable components, non-sulfonated but solfonatable components and non-sulfonatable components. Upon standing, such acidic reaction product mixtures tend to change in composition and properties, apparently because some residual $SO_3$ or degenerate specie thereof is present within the reaction products and gradually reacts with sulfonatable components therein, although other theories or explanations for this apparent instability may be equally valid. Nevertheless, such non-homogeneity and instability limits the extent of usefulness for such reaction products and often necessitates further processing before a final product is attained which is suitable for various industrial and commercial purposes, such as enhanced oil recovery in diverse reservoir environments.

U.S. Pat. No. 2,928,867 suggests that stable alkaryl sulfonates (i.e., dodecylbenzene sulfonates) may be prepared by sulfonating pure or relatively pure dodecylbenzene or postdodecylbenzene (a mixture of mono-and di-alkylbenzenes) with $SO_3$ under sulfonation conditions, cooling the resulting alkaryl sulfonic acid, adding a small amount of water to the cooled sulfonic acid over a relatively brief period of time and then neutralizing the resultant sulfonic acid with caustic to obtain a pH-stable alkaryl sulfonate useful in detergent formulations. However, this prior art patent is silent as to enhanced oil recovery techniques or any surface-active agents useful in such oil recovery processes.

SUMMARY OF THE INVENTION

The invention provides an economical and novel composition of matter which exhibits improved and stable properties useful in enhanced oil or petroleum recovery, a method of producing such composition of matter and a method of enhanced petroleum recovery utilizing such composition of matter.

In accordance with the principles of the invention, a select petroleum oil feed stock, such as a topped crude, a heavy vacuum gas oil or some other partially refined or whole crude is admixed with a small amount (i.e., about 0.5% to about 15% by weight of petroleum oil feed stock) of an additive, such as comprised of an unsulfonatable organic radical portion having an average molecular weight range extending from about 55 to 6000, having a boiling point in the range of about 100° C. to 260° C. and a preponderance of such radicals each having attached thereto at least one portion replaceable by a sulfo group and at least one moiety selected from the group consisting of an aromatic nucleus, an olefinic carbon pair and an oxygen atom directly bonded to a carbon atom by at least one bond (i.e., a $C_6$ to $C_{28}$ alcohol material, such as an oxo alcohol still bottom) and then the resultant additive-feed stock mixture is sulfonated with $SO_3$ under sulfonation reaction conditions. A small amount (i.e., about 0.5 to 20% by weight of the resultant crude acidic reaction mixture) of water is then added to the resultant sulfonation reaction mixture and the sulfonation reaction mixture-water mixture is held at an elevated temperature (i.e., in the range of about 50° to 150° C.) for a relatively brief period of time (i.e., ranging from about 2 to 60 minutes) and then neutralized with a base. The resultant petroleum sulfonate product, which may first be subjected to an extraction process, if desired, is then formulated into a micellar system, such as a microemulsion or the like system and injected into select petroleum reservoirs for enhanced oil recovery.

By practicing the principles of the invention, one is able to attain enhanced oil recovery yields on the order of 60% to 90% or more, as compared to typically lower yields obtained with similar petroleum sulfonates which have been non-water treated before neutralization by conventional prior art techniques.

The novel stabilized petroleum sulfonate products obtained by the practice of the invention comprise, on a 100 organic weight percent total weight basis (a) from about 2 to 90 weight percent of substantially non-sulfonated hydrocarbon material;

(b) from about 0 to 50 weight percent of non-sulfonated but sulfonatable hydrocarbon material;

(c) from about 5 to 98 weight percent of monosulfonated hydrocarbon material;

(d) from about 0 to 50 weight percent of polysulfonated hydrocarbon material; and (e) from about 0.5 to 15 weight percent of an additive.

Accordingly, a primary object of the present invention is the provision of a stabilized relatively homogeneous petroleum sulfonate product which comprises sulfonated and non-sulfonated components, a method of attaining such sulfonate products and a method of enhanced subterranean oil recovery utilizing such sulfonated products.

Other and further objects, aims, purposes, advantages, uses and the like of the present invention will be apparent to those skilled in the art from the following description of preferred embodiments thereof, although variations and modifications may be effected without departing from the spirit and scope of the novel concepts of the invention.

DETAILED DESCRIPTION

Sulfonation

During the course of the instant disclosure, it is to be understood and intended that the terms "sulfonation", "sulfonated" or equivalent, apply herein to any reaction which results in the substitution of a sulfo radical in a molecule of an initial starting material. Thus, it will be understood that these terms also encompass any sulfation reactions which may also be occurring, for example, with a petroleum oil feed stock containing a component having one or more hydroxy radicals per molecule. The hydroxy group of such component may or may not tend to react with sulfur trioxide. Thus, for example, such component-types as naphthols or substituted naphthols, are apparently characteristically sulfonated through the ring radical rather than through the hydroxy radical in the practice of the method of this invention. Similarly, the petroleum oil feed stock components capable of reacting with a sulfonating agent, such as sulfur trioxide, are sometimes referred to as sulfonatable or sulfatable components, and, more generally, as sulfonatable or reactable components, and it will be understood that these terms all refer to petroleum oil components capable of reaction with a sulfonating agent.

Petroleum Oil Feed Stock

The petroleum oil feed stocks used as starting materials in the practice of this invention can be any petroleum oil feed stock known in the art. For example, gas oils, topped crude oils, heavy vacuum gas oils, lubricating oils, selected fractions recovered from lube oil treating processes, selected fractions from paraffinic, naphthenic, whole crudes, lightly distilled crudes, mixed base crudes or mixtures thereof. As workers in the art are well aware, extensive characterizations of petroleum oil stocks and/or crudes are availabe, for example, see "Evaluation of World's Important Crudes" (The Petroleum Publishing Co.), 1973, which contains a compilation of various characteristics of geographically diverse crude oils, while C. J. Thompson et al, "Hydrocarbon Processing—Analyzing Heavy Ends of Crude", September 1973, pages 123–130, characterizes the higher boiling fractions of five different crude oils of different chemical composition and geological origin. Similarly, the characteristics of various fractions or products obtained in refining petroleum or crude oil is known, for example, see W. L. Nelson, "Petroleum Refining Engineering", 4th Ed. (McGraw-Hill Book Co.). However, for purposes of the invention, such extensive characterizations are generally not required. Any available petroleum oil feed stock which contains sulfonatable components therein may be used in the practice of this invention. Thus, the petroleum oil feed stocks may be any natural material, or blend of natural and synthetic petroleum oils, including whole or partially refined natural crude oils, or portions thereof, such as synthetic oil stocks and mixtures of any of the above. The petroleum oil feed stocks may also contain waxes or may be partially or completely dewaxed petroleum oils. Another petroleum feed stock which may be employed as a starting material is a raffinate obtained in solvent refining of petroleum fractions. One may carry out such refining or extraction with various cyclic solvents, phenols, methyl ethyl ketones, liquid $SO_2$, etc. Both the resultant raffinate and the gripped extract may be subjected to sulfonation in accordance with the principles of the invention.

In many instances, petroleum oil feed stocks useful as starting materials in the invention exhibit at $-20°$ to $1400°$ F. ($-29°$ to $760°$ C.) corrected atmospheric boiling range (although higher and lower boiling feed stocks may also be used) and have an API gravity ranging between about $5°$ to $60°$ at $60°$ F. ($15.6°$ C.). Preferred petroleum oil feed stocks also include crudes which have aromatic portions with molecular weights in the general range of about 200 through about 1000 and more preferably in the range of about 250 through about 800, while the most preferred range is about 250 through 500. The amount of aromatic compounds or portions within a crude oil useful in the practice of this invention is generally about 10% to 95% (although purified synthetic feed stocks having 98% or more aromatic compounds therein are also useful in the practice of the invention), and more preferably about 20 to 80%, and most preferably about 25 to 75%, by weight of aromatics, as defined in the American Petroleum Institute Project 60 Reports 4–7 under "Characterization of Heavy Ends of Petroleum". Preferred petroleum oil feed stocks include Texas crude oil, Libyan crude oil, Louisiana crude oil, California crude oil, Wyoming crude oil, Michigan crude oil, Illinois crude oil, Ohio crude oil, Oklahoma crude oil, Mississippi crude oil, Canadian crude oil, as well as various other geographically diverse crude oils. Preferred petroleum oil feed stocks also include crude oils having aromatic portions thereof which have a proton ratio of aliphatic radicals or compounds to aromatic radicals or compounds of approximately 3 through 20 and more preferably about 4 through 18. Lightly distilled or topped crude oils, for example, where at least a portion of the hydrocarbons boiling below about $680°$ F. ($320°$ C.) have been removed, may also be used as the feed stock. Of course, mixtures of various crude oils, or portions thereof, as well as blends may also be used as feed stocks in the practice of the invention.

The petroleum oil feed stocks may also be a material which is derived by subjecting a petroleum crude to one or more of the following general types of refinery processes, including thermal or catalytic processes: topping, reforming, cracking, alkylation, isomerization, polymerization, desulfurization, hydrogenation, dehydrogenation, distillation (including atmospheric and vacuum), sweetening, etc. Petroleum oils containing substantial amounts of aromatic compounds, naphthenic compounds and/or unsaturated compounds are also useful in the practice of the invention. Likewise, straight run or refinery naphtha streams may be sulfonated in accordance with the principles of the invention, although higher boiling fraction feed stocks are generally preferred. Also, petroleum oil stocks can be prepared by admixing together two or more different partially refined petroleum oils including crude oils so as to obtain, for example, some particular desired starting petroleum oil stock having a particular content of sulfonatable components and/or having a particular boiling range.

A wide variety of sulfonatable or reactable compounds or materials are characteristically present in various petroleum oil feed stocks, including aromatics, olefins, as well as alicyclic and aliphatic hydrocarbon compounds (and it is recognized that some alicyclic and aliphatic paraffins may be less reactable than some other compounds), etc., all of which various classes of materials are sulfonatable to variable degrees in accordance with the principles of the invention.

In order to estimate the amount of reactable or sulfonatable components in a selected petroleum oil feed stock, one may resort to a number of known procedures. For example, one may utilize an ASTM process, such as ASTM Test No. D848-62, which generally comprises feeding a petroleum oil feed stock with an excess of fuming (20%) oleum and then measuring the remaining layer of oil. A number of other methods, for example, a silica gel chromatography method, may be used in place of the exemplary method set forth above to determine a more or less approximate content of sulfonatable components in any petroleum oil feed stock (ASTM Test No. D2007).

In summary, a petroleum oil stock useful as a starting material in the practice of the present invention is characterized by:

(A) having an API gravity ranging from about $5°$ to $60°$ and somewhat more preferably from about $10°$ to $40°$ at $60°$ F. ($15.6°$ C.);

(B) having a boiling point in the range of about $-20°$ to $1400°$ F. ($-29°$ to $760°$ C.) and somewhat more preferably from about 500° to 1100° F. (260° to 600° C.), corrected atmospheric; and (C) containing from about 10 to 95 weight percent (100 weight percent total stock basis) of sulfonatable components.

Preferred starting petroleum oil feed stocks may contain initially not more than about 3 to 10 weight percent (100 weight percent total stock basis) of combined elements selected from the group consisting of oxygen, sulfur and nitrogen and generally molecules containing such elements are not sulfonatable to any appreciable extent. Those skilled in the art will appreciate that petroleum oil feed stocks may also commonly contain quantities of water and of hydrocarbon molecules having incorporated thereinto atoms of oxygen, sulfur and nitrogen. In general, for purposes of the present invention, it is not necessary to eliminate such combined elements from a starting petroleum oil feed stock for use in the present invention, but it is preferred that a starting petroleum oil feed stock contain not more than the above indicated quantities of these elements.

Additives

In general, additives employed in this invention are organic species characterized as organic radicals, a preponderance of which have attached thereto at least one proton replaceable by a sulfo group and at least one moiety selected from the group consisting of an aromatic nucleus, an olefinic carbon pair, and an oxygen atom directly bonded to a carbon atom by at least one bond. Typically and preferably, a given additive specie and/or molecule may have attached thereto a plurality of such protons and moieties and a mixture of different type additives may also be utilized. The presence of one or more of the additives in a liquid petroleum feed stock being subjected to a sulfonation reaction by this invention appears primarily to promote the compatibility of sulfonated oil components with unsulfonated or unsulfonatable oil components under reaction conditions, though there is no intent herein to be bound by theories or appearances. An apparent major function of an additive within the reaction system is to promote compatibility of reactants and reaction products under reaction conditions (and it is to be noted that these additives, after sulfonation, have other functions in ultimate products of this invention). The additives during the sulfonation reaction seem to maintain an adequate solution or dispersion of petroleum oil components (reactants and reaction products) in such a way that adequate heat exchange and/or temperature control is effected between the sulfur trioxide or gas phase, the petroleum oil feed stock additive mixture or liquid phase and the heat exchange surfaces and/or reactor walls under the reaction conditions. Thus, the additives may be designated "compatibility promoting additives" and allow one to achieve an effective means of process and product control. The absence of one or more additive in an oil feed stock sulfonation process appears to result in gross component separation, lack of liquid compatibility, lack of uniform heat control, excessive polysulfonation, excessive sludge formation and an inability to maintain process control or reaction stability (although it is to be noted that certain low viscosity starting petroleum feed stocks and/or petroleum feed stocks mixed with solvents or diluents therefor, such as ethylene dichloride, trichloroethane, nitrobenzene, nitropentane, and the like may be at least partially sulfonated without the presence of a significant amount of additives). Nevertheless, improved reaction products and reaction control apparently can be attained when at least some additives are present with the oil feed stock in the reaction zone. The additives also appear to reduce undesired oxidation of the oil feed stock, so that substantially less of, for example, reactant gaseous sulfur trioxide is lost via reduction to sulfur dioxide. For example, in prior art processes of sulfonating petroleum oil feed stocks with gaseous or liquid $SO_3$, as much as about 50% of the $SO_3$ is reduced to $SO_2$, depending on the degree of $SO_3$ input, oil type, etc. However, by following the principles of the invention, the loss of $SO_3$ is kept relatively low.

Also, the common prior art over-reaction of sulfonatable components in oil feed stock is apparently reduced by the presence of the additives so that less polysulfonates may be produced in the reaction products if so desired. In other words, the additives apparently provide an operator with a means for achieving some desired and substantially controlled ratio of monosulfonates to polysulfonates and equivalent weight distribution. For example, when a petroleum oil feed stock is divided into two portions for sulfonation, one of which is admixed with an additive and the other portion is sulfonated as such without an additive, and both such portions sulfonated under otherwise identical conditions and $SO_3$ treat levels, the products recovered in each instance have different equivalent weights and monosulfonate contents. The equivalent weight, ($\overline{\epsilon\omega}$), as determined by a silica gel analysis (ASTM Test No. D855-56) is almost invariably higher for the sulfonation product recovered from the portion containing the admixture of additive and oil feed stock. The monosulfonate content, as determined by a paratoluidine analysis is also generally higher for the product recovered from the portion containing the admixture of additive and oil feed stock. These results demonstrate that the addition of an additive to a petroleum oil feed stock undergoing sulfonation reduces the amounts of polysulfonates or low $\overline{\epsilon\omega}$ monosulfonate by-products (which are generally undesirable), as compared to prior art sulfonation of petroleum oil feed stocks without additions of additives. When an additive is present, the mono to disulfonate content in the active portion of the resultant product is generally in the 3:1 to 50:1 ratio whereas without an additive, the ratio of mono to disulfonate ranges up to about 1:1. At optimum $SO_3$ treat levels, sulfonation of an additive containing petroleum oil feed stock yields a product which is superior to a reaction product from a nonadditive containing oil feed stock (i.e., a mahogany sulfonate). This superiority is shown by the higher $\overline{\epsilon\omega}$ and greater monosulfonate content in sulfonation products of an additive containing petroleum oil feed stock. At higher than optimum $SO_3$ treat levels, over-sulfonation occurs and a lower $\overline{\epsilon\omega}$ and lower monosulfonate content results. Accordingly, by a judicious selection of the amount of additive utilized and the $SO_3$ treat level utilized, an operator readily controls the amount of mono and polysulfonate in the ultimate sulfonation product.

The additives also tend to promote compatibility, solubilization, dispersion and/or coupling of the reaction products (sulfonated petroleum) with unreacted starting petroleum oil feed stock to yield a homogeneous or substantially homogeneous solution, dispersion and/or micellar solution, under sulfonation reaction conditions. While the exact chemical and/or physical functions of the additive described herein may not be fully understood, it is hypothesized that the additives somehow promote compatibility between unsulfonatable and/or unsulfonated components in admixture with an oil feed stock and the sulfonated components thereof. Observations taken during a film sulfonation reaction between unadulterated petroleum oil feed stocks and diluted gaseous sulfur trioxide lead to tentative conclusions that, as the sulfonatable components in the petroleum oil feed stocks become sulfonated, such sulfonated components tend to form an outer layer or boundary on the film or in a reaction mixture. At such outer location, the sulfonated components may be exposed to further sulfur trioxide and may tend to overreact, causing charring, polysulfonate formation, etc. Similar observations taken during a sulfonation reaction between a petroleum oil feed stock-additive mixture and diluted gaseous sulfur trioxide do not show any such outer layer, and it appears that the resulting sulfonated components remain within the film as a homogeneous mixture, a dispersion, or possibly an emulsion with the non-sulfonated components in the film, so that overreaction is substantially prevented or minimized, and the amount of polysulfonates in the ultimate product is characteristically materially reduced.

Of course, other explanations may be advanced as to the reason why the additives described herein promote increased yield of sulfonates during sulfonation of petroleum oil feed stocks and there is no intent to be bound herein by any theory or possible explanations.

As explained hereinabove, the additives also appear to enhance the attainment of a desired equivalent weight ($\bar{\epsilon\omega}$) range within the reaction product, which may be a mixture of various sulfonated and non-sulfonated compounds. The equivalent weight or $\bar{\epsilon\omega}$ of a sulfonate may be defined in the case of a salt as the combining weight thereof, i.e., the weight of sulfonate containing one gram atom of a cation (generally ammonium or sodium). For monosulfonates, the $\bar{\epsilon\omega}$ or combining weight is identical with the molecular weight. In the case of disulfonates, the combining weight is just one-half of the molecular weight but is nevertheless referred to as the equivalent weight thereof. In other words, the $\bar{\epsilon\omega}$ of petroleum sulfonate or of the reaction products may be defined as the sulfonate molecular weight divided by the average number of sulfonate groups per molecule. The $\bar{\epsilon\omega}$ indicates the relative amount of monosulfonation and polysulfonation, i.e., the $\bar{\epsilon\omega}$ becomes lower as the polysulfonation increases.

The additives of the invention may be used as mixtures with suitable solvents or as mixtures among themselves. The additives themselves may undergo sulfonation or sulfation reactions and may result in a complex mixture with the other reaction products and may be usable as such or may be further processed before use thereof. Additives useful in the practice of this invention are chosen from a wide variety of chemicals, identified hereinafter, and which have the ability to effectuate at least one or more of the above discussed functions, such as promoting compatibility between sulfonated and unsulfonated and/or non-sulfonated oil feed stock components, decreasing and controlling viscosity during the sulfonation reaction, providing an adequate solution or dispersion of oil components (reactants and reaction products) in such a way that adequate or "stabilized" heat control and/or heat exchange is effected and thus providing a means of maintaining process control. Further functions of additives include: providing an improved sulfonation reaction; substantially increase the yield of petroleum sulfonates over the heretofore available processes; providing a control so that almost any desired ratio of monosulfonates to polysulfonates can be achieved with low amounts of undesirable salts; promoting the formation of adequate solutions/dispersions of reactants and reaction products under sulfonation and ultimate use (for example, in soluble, dispersion or micellar systems) conditions; providing a substantially theoretical yield of sulfonates from various oil feed stocks; providing improved operability in various continuous, batch, quasi-batch or quasi-continuous processes in various diverse apparatuses; reducing undesirable oxidation of the oil feed stock; provide a more efficient utilization of $SO_3$ so as to produce higher conversion to sulfonate activities as compared to reactions without additives; providing a means of reducing or controlling viscosity of the sulfonation mixture; provide a means of effecting improved continuous sulfonation processes; reducing charring, oxidation and polysulfonation in the sulfonation reaction; reducing or preventing plugging or otherwise damaging reaction systems and components; being useful with an extremely wide variety of petroleum oil feed stocks; being adaptable to a wide variety of sulfonation processes and apparatuses; providing a means of achieving product composition control, i.e., by varying as desired the ratio of mono to polysulfonate and minimizing sludge formation; enhancing post-reactor digestion by reacting with any residual $SO_3$ or $H_2SO_4$ present in initial reaction products; providing an option to eliminating the need for extraction; providing a means for reacting $SO_3$ with oil feed stock at lower temperatures in comparison to reactions without additives; contributing to phase separation of acid from unreacted oil in the reaction products; (capable of being hydrolyzed, if sulfated, so as to be removable from the reaction products if desired); capable of being functional within an enhanced oil recovery system, particularly when the sulfonation reaction products are first water-treated prior to neutralization or formulation into an oil recovery system providing a basis for solvent-free sulfonation; providing petroleum sulfonates which exhibit an enhanced oil recovery property; etc. Additive systems also apparently provide an important means of maximizing both high monosulfonation and commensurate sulfonate equivalent weight.

Generally, these additives comprise relatively high boiling organic compounds including unsaturated aliphatic hydrocarbons, substituted and unsubstituted aromatics, olefins, oxygen-containing compounds, esters (especially high boiling esters), ethers, ether esters (especially high boiling ether esters), certain catalytic phase oils, polymer distillation residues, mixtures of alkylated benzenes and naphthalenes, mixtures thereof, alkoxylated derivatives of such compounds, and the like. These additives generally comprise organic compounds generally containing from 2 through 30 carbon atoms within their main hydrocarbon chain and may contain more carbon atoms, for example, in side chains or in alkoxylated additives condensed onto the main compound or radical. Such organic compounds are of a type which promote compatibility of unsulfonated (sulfonatable and non-sulfonatable) petroleum oil feed stocks with sulfonated components during $SO_3$ reaction conditions. Compounds of this type generally have boiling points in the range from about 212° to 932° F. (about 100° to 500° C.) or higher, depending upon the degree of substitution, if any. Additionally, such compounds generally are comprised of unsulfonatable organic radicals having an average atomic weight in the range of from about 55 through 6000, and somewhat more preferably in the range from about 75 through 1000, and most preferably in the range of from about 100 to 350 (excluding any alkoxy or the like units, which may range up to about 1000 or more, attached thereto) and a preponderance of such organic radicals each have attached thereto at least one proton replaceable by a sulfo group and at least one moiety selected from the group consisting of an aromatic nucleus, an olefinic carbon pair, and an oxygen atom directly bonded to a carbon atom by at least one bond.

Preferred groups of organic additives useful in the practice of the invention are selected from the clases consisting of alcohols, oxygen-containing compounds, hydroxy-containing compounds, substituted and unsubstituted hydrocarbons, high boiling esters, high boiling ethers, high boiling ester ethers, aromatic compounds, fatty acids and derivatives thereof, olefins, ketones, alkaryl compounds and mixtures thereof. A preferred class among this group is the oxygen or hydroxy-containing compounds, both of which are sometimes referred to hereinafter as "oxygenated" or oxygen-containing compounds.

A species of the oxygenated compounds (which include the hydroxy-containing compounds) useful in the practice of the invention comprise aliphatic alcohols. Typical aliphatic alcohols useful in the practice of the invention are those which contain at least 4 carbon atoms per molecule (although $C_1$ to $C_3$ aliphatic alcohols may be used when such low molecular weight alcohols are alkoxylated with a plurality of alkoxy units) and preferably are $C_6$ to $C_{28}$ aliphatic alcohols. Mixtures of aliphatic alcohols (some of which may be alkoxylated) may also be used in the practice of the invention. For example, one may employ octyl alcohol, nonyl alcohol, decyl alcohol, hexyl alcohol, octadecyl alcohol, dodecyl alcohol, lauryl alcohol, myristyl alcohol, palmityl alcohol, stearyl alcohol, etc. or mixtures thereof. A particularly useful aliphatic alcohol is a tallow alcohol (which is a mixture of $C_{14}$ to $C_{18}$ fatty alcohols).

Another useful species of oxygen-containing or oxygenated compounds comprises phenolic compounds which include substituted phenolic compounds. Typical phenolic compounds comprise phenol, octyl phenol, nonyl phenol, resorcinol, etc. as well as phenol compounds having one or more $C_1$ to $C_{16}$ alkyl thereon, $C_2$ to $C_4$ alkoxylated phenols (including alkoxylated alkyl phenols), polyalkoxylated (including polyalkoxylated polyalkyl phenols) phenol including mixed polyalkoxylated phenols, i.e., ethylene oxide-propylene oxide units, or mixtures thereof.

A further useful species of oxygen or hydroxy-containing compounds comprises glycol and glycerol compounds, such as propylene glycol, butylene glycol, ethylene glycol, diethyl glycerol, etc. all of which may be alkoxylated, if desired.

Yet a further useful species of oxygen or hydroxy-containing compounds comprises organic acids, such as $C_4$ to $C_{22}$ fatty acid, which may also be alkoxylated, if desired.

A preferred species of oxygenated (hydroxy-containing) compounds useful in the practice of the invention are commercially available high-boiling alcohol-containing materials known as oxo alcohols or oxo bottoms and more particularly as oxo alcohol still bottoms, oxo alcohol distillation residue, oxopolymer products or oxo alcohol polymer bottoms. The preparation and description of these alcohol materials is known, for example, as set forth in a book entitled "Higher Oxo Alcohols" by L. F. Hatch, Enjay Company, Inc., 1957, the disclosure of which is incorporated herein by reference. The term "oxo alcohol" is used in the art as descriptive of the type of process employed in producing these alcohols synthetically. Alcohols having the desired functionality can also be obtained from natural sources as well as from available synthetic processing means, and functionality is not dependent on the source or synthesis process. Generally, oxo alcohols comprise a complex mixture of various alcohols, ether alcohols, esters, soaps, etc., for example, as described by E. H. Bartlett et al in an article entitled "Oxo Ether Alcohols", published in Industrial and Engineering Chemistry, Vol. 51, No. 3, March 1952, the disclosure of which is incorporated herein by reference. Commercially available oxo alcohols include those in the $C_4$ to $C_{18}$ range and two particularly attractive oxo alcohols are the $C_8$ and $C_{10}$ materials, both of which are mixtures of isomers produced by the oxo process from branched $C_7$ and $C_9$ olefins. A typical oxo alcohol still bottom of this type which is useful in the practice of the invention has the following composition:

| Component | % By Weight |
| --- | --- |
| Octyl alcohol | 2–20 |
| Nonyl alcohol | 5–40 |
| Decyl and higher boiling materials* | 25–90 |
| Esters | 20–80 |

*Ether alcohols, saturated and unsaturated ethers, mixtures thereof, as well as other oxo reaction by-products.

Another oxo alcohol still bottom which is an excellent additive useful in the practice of the invention has the following composition:

| Component | % By Weight |
| --- | --- |
| Octyl alcohol | 5 |
| Nonyl alcohol | 10 |
| Decyl and higher boiling materials | 35 |
| Esters | 45 |
| Soaps | 5 |

*Ether alcohols, saturated and unsaturated ethers, mixtures thereof, as well as other oxo reaction by-products.

Any of the above oxygen or hydroxy-containing compounds may also be alkoxylated by a reaction with a select number of mols, say about 1 to 200 mols, of a $C_2$–$C_4$ alkoxide, i,e., ethylene oxide, propylene oxide, butylene oxide, an ethylene oxide-propylene oxide unit or mixtures thereof.

Another class of additives useful in the practice of the invention comprise high boiling unsaturated (olefins) branched or straight-chain hydrocarbons (i.e., having a boiling point in the range of about 100° to about 500° C.). Generally, these compounds comprise $C_4$ to $C_{28}$ hydrocarbons and preferably are $C_8$ to $C_{22}$ hydrocarbons, such as, for example, $C_{14}$ or $C_{18}$ α-olefins, mesityl oxides, tetradecene, octocosene, docosene, octodecene, etc., or mixtures thereof.

Yet another useful class of additives useful in the practice of the invention is high boiling ethers, i.e., having a boiling point in the range of about 100° to about 500° C. Typical members of this class are glycol ethers, such as available under the trademark "CELLOSOLVE" from Union Carbide Corporation, and which include such ethers as 4-methoxy butanol, 2-ethoxy ethanol, 2-propoxy ethanol, 2-butoxy ethanol, etc. Other typical ethers useful herein are those available under the trademark "CARBITOL" from Union Carbide Corporation and which include such ethers as diethylene glycol ethyl ether, diethylene glycol butyl ether, etc. The preferred glycol ethers include $C_4$ to $C_6$ glycol ethers, such as diethylene glycol, etc.

Another class of additives useful in the practice of the invention is high boiling ether esters (i.e., having a boiling point in the range of about 100° to 500° C.), such as available under the trademarks "CARBITOL" or "CELLOSOLVE". Typical materials of this type are "CARBITOL" acetates such as methoxy diethylene glycol acetate or "CELLOSOLVE" acetates such as methoxy ethyl acetate, butoxy ethyl acetate, etc.

Yet another class of additives useful in attaining an improved degree of reaction between petroleum oil feed stocks and gaseous sulfur trioxide is the alkaryl compounds, typically comprising $C_7$ to $C_{30}$ compounds having a boiling point in the range of about 100° to 500° C. Typical materials of this type include $C_1$ to $C_{20}$ alkyl substituted benzenes, such as dodecylbenzene, cumene, thymol (p-propyl-m-cresol), etc.

An additional class of additives useful in the practice of the invention is esters. Typically, preferred esters having boiling points in the range of from about 100° to 500° C. and comprise $C_1$ to $C_4$ alkyl esters of $C_4$ to $C_{22}$ aliphatic carboxylic acids, for example, methyl, ethyl, etc., esters of octyl, nonyl, decyl, lauryl, myristyl, palmityl, stearyl, etc. acids or mixtures thereof. A preferred group of such alkyl ester acids are the methyl esters of $C_8$ to $C_{18}$ fatty acids, and, of these, the methyl esters of $C_8$ to $C_{10}$ and $C_{10}$ to $C_{18}$ are extremely useful. Useful esters may also be produced by reacting the above $C_6$ to $C_{20}$ aliphatic acids with the $C_6$ to $C_{28}$ aliphatic alcohols described earlier, all of which may be alkoxylated, if desired.

Further additives useful in the practice of the invention include catalytic cycle oil, such as defined in U.S. Pat. No. 3,317,422 (column 1, lines 55-72), which is incorporated herein by reference, ultraformer polymer bottoms (a known commercially available material principally comprised of mixtures of alkylated benzenes and naphthalenes, and mixtures thereof), as well as other like materials.

In summary, an additive useful as a starting material in the practice of the present invention is characterized by:

(A) being comprised of unsulfonatable organic radicals possessing an average molecular weight from about 55 to 6000;

(B) having a boiling point in the range from about 100° to 500° C. (212° to 932° F.) corrected atmospheric pressure, and (C) a preponderance of such radicals each having attached thereto at least one proton replaceable by a sulfo group and at least one moiety selected from the group consistng of an aromatic nucleus, an olefinic carbon pair, and an oxygen atom directly bonded to a carbon atom by at least one bond. (Of course, polyfunctional molecules having a plurality of such protons and moieties attached thereto are also included as are various blends of additives.)

Additives useful in the present invention can initially be admixed with other organic materials, such as alkane hydrocarbons, halogenated hydrocarbons, and the like, which do not appear to undergo sulfonation when exposed to sulfur trioxide. Preferably at the time of use in the practice of this invention, however, an additive composition contains a preponderance (i.e., not less than about 60 weight percent total additive composition basis) of at least one additive characterized as above.

Water

In general, the water employed in this invention may comprise any available relatively pure water, including raw tap water, demineralized or softened water, deionized water, distilled water, etc., as well as other forms of water, such as steam. In selecting a water source, it is advisable to avoid water containing a relatively high concentration of polyvalent ions therein, such as calcium or magnesium ions, although water with a relatively moderate or low concentration of polyvalent ions may be used, if desired.

A relatively small amount of water, generally about 0.5 to 20% by weight of crude reaction mixture (as will be appreciated, higher amounts of water may be used without notable detriment, providing that the economics of handling additional material are taken into account; for example, additional amounts of water might be desired if a dilute oil recovery formulation is made directly) is added, as by injection, into the hot crude sulfonation reaction mixture obtained from containing $SO_3$ with a petroleum oil feed stock-additive mixture. After a brief digestion or contact period of about 2 to 60 minutes at an elevated temperature of about 50° to 150° C., neutralization is effected by mixing the water-treated, sulfonation reaction mixture with a sufficient amount of a base, such as a 50% NaOH solution to attain a pH in the range of about 3 to 12 and preferably in the range of 6 to 11.

As demonstrated hereinafter, the order of water and base addition is important and yields sulfonate materials having improved oil recovery properties not available with somewhat similar sulfonate materials treated in some other manner. The exact nature of the water treatment step is not presently fully understood, however, it is noted that water-treated sulfonation reaction mixtures are capable of forming better micellar systems (i.e., requiring less of a co-surfactant, such as an alcohol, for example, hexanol), exhibit a higher average equivalent weight, retain relatively low interfacial tension ($10^{-2}$ to $10^{-4}$ dynes/cm), exhibit a lower overall viscosity and provide improved phase stability and homogeneity, especially for the acidic reaction mixtures, and, most important, provide improved oil recovery when further processed, formulated into an oil recovery system and injected in a subterranean petroleum bearing formation via a slug formulation.

Sulfonation Process Details

In proceeding along the principles of the invention and in accordance with one of the more preferred embodiments of the invention, the petroleum oil feed stock is first mixed with an additive. In general, mixtures employed in the present invention comprise from about 0.5 to 15 weight percent of an additive, and from about 85 to 99.5 weight percent of a petroleum oil stock, on a 100 weight percent total mixture basis. Preferably, a mixture employed in the present invention comprises from about 2 to 10 weight percent of an additive and from about 98 to 90 weight percent of a petroleum oil stock on a 100 weight percent total mixture basis.

Preferably, in one mode, a film of such mixture is fed to a reaction zone of a reactor, such as a tubular reactor. A selected additive may be added if desired from a source thereof to an already formed film of oil feed stock prior to or simultaneously with $SO_3$ contacting or a select additive may be mixed with an oil feed stock prior to being fed, in film form, to a reaction zone. The mixture or just the petroleum oil feed stock may be heated prior to $SO_3$ contact, if desired.

The reaction zone generally is one compatible with the reaction of gaseous $SO_3$ (sulfur trioxide) and a sulfonatable material. A wide variety of existing processes and apparatuses incorporate and utilize suitable reaction zones. Examples of such prior art processes and apparatus include U.S. Pat. Nos. 2,697,031; 2,768,199; 2,923,728; 3,056,831; 3,270,038; 3,328,460; 3,427,342; 3,438,742; 3,438,743; and 3,438,744.

The contacting of sulfur trioxide with a mixture of petroleum oil stock and additive as above characterized is affected generally at a temperature ranging from about 25° to 200° C. (about 77° to 392° F.) although if solvents, such as liquid $SO_2$, are utilized, lower temperatures may be used. In the reaction from about 5 to 40 parts by weight of sulfur trioxide are contacted typically with each 100 parts by weight of the (essentially moisture-free) mixture comprised of petroleum oil stock and additive being sulfonated. The total time of contacting of sulfur trioxide with such mixture is at least sufficient to sulfonate not less than about 10 weight percent of the total sulfonatable components present in the starting petroleum oil stock.

Preferably, such contacting is continued for a time at least sufficient to produce a sulfonated composition which is then water-treated so as to comprise a composition of this invention, as hereinafter defined.

Since temperature, time and pressure conditions are not critical and may be readily adjusted by an operator in accordance with a particular feed stock, reaction apparatus, process or desired end product, all such conditions will sometimes be referred to herein as "time-temperature-pressure conditions" sufficient to form sulfonation products.

One excellent and commercially feasible method for continuous sulfonation is set forth by Knaggs et al in U.S. Pat. No. 3,169,142 (owned by the instant assignee), the disclosure of which is incorporated herein by reference. The method thereof, which will be described in further detail hereinafter is improved by the instant invention, particularly in relation to sulfonation of petroleum oil feed stocks. However, it will be appreciated that the invention may also be practiced by various other sulfonation methods, such as batch, cascading, quasi-continuous, etc.

Generally, the contacting time varies from about 0.001 seconds or less to about 1800 seconds or more, depending on the type of apparatus used, the desired degree of sulfonation, the extent of recycling (if any) of the reactants and/or reaction products, etc.

As set forth earlier, a mixture of starting petroleum oil feed stocks and additive is fed, in a liquid form, which, in the preferred embodiment under discussion, comprises flowing a film of such mixture to a reaction zone of a reactor. In such a preferred embodiment, the liquid film of petroleum feed stock and additive is supported on a supporting and confining heat exchange surface defining the reaction zone. An apparatus which includes such a surface may comprise a tubular or multiple tube reactor, such as described in the above referenced Knaggs et al U.S. Pat. No. 3,169,142 generally known as a falling film reactor and/or a more complex wiped film reactor, such as shown in U.S. Pat. No. 3,427,342. Of course, in other processes, such as for example, in a batch $SO_3$ sulfonation process, the liquid mixture is simply fed to a reaction vessel which may include either a heat exchange surface along select portions thereof, or a cyclic looped external heat exchanger.

The sulfonation reaction of this invention can be carried out using a gaseous $SO_3$, optionally admixed with an inert gas, such as nitrogen or air. Generally, the ratio of inert gas to gaseous $SO_3$ falls within the range of from about 3:1 to 75:1 and preferably from about 5:1 to 50:1. In certain instances, it may be desirable to utilize liquid $SO_3$, admixed with or without a liquid or gas diluting agent, such as for example, $SO_2$ refined light paraffinics, light crude oil distillates, air, nitrogen, pentane, and the like, and such a liquid mixture is within the scope of the invention. An effluent diluent-gas can be recycled and $SO_3$ added thereto to thereby provide a closed system. Further, if desired, $SO_3$ may be utilized per se whether in liquid or gaseous form, although from a point of safety and reaction control, it is preferable to utilize a mixture of gaseous $SO_3$ and an inert gas. The gas mixture is preferably caused to impinge on the liquid petroleum-additive mixture and readily reacts with the sulfonatable components of such liquid as soon as sulfur trioxide comes in contact with at least some of the reactable components present in the liquid. This reaction is exothermic and good heat exchange capabilities may be required in the reaction system, such as by providing a reaction surface having a heat exchange means associated therewith or by providing an operable external heat exchange system.

The amount of additive present in the reaction zone generally is at least about 0.5% by weight based on the weight of starting petroleum feed stock. Generally, the amount of compatibility promoting additive utilized in accordance with the principles of the invention range from about 0.5% to about 15% by weight and a practical additive dosage is about 0.5% to 5% or 2% to 10% (same basis). As those skilled in the art will appreciate, the exact or optimum amount of additive utilized with a selected petroleum oil feed stock is dependent upon a wide variety of variables, such as characteristics of the oil feed stock, desired degree of sulfonation, availability of a select additive, etc., and a specific amount for use in a given system may be readily determined by those skilled in the art.

The selection of particular reaction conditions, such as time, temperature, pressure, etc., depend upon a number of process variables, such as characteristics of petroleum oil feed stock, the amount and type of additive, the apparatus employed, the characteristics of the formed products, etc. Generally, the sulfonation is conducted using temperatures in the range of about 25° to 200° C. (77° to 392° F.) and somewhat more preferably in the range of about 50° to 140° C. (122° to 248° F.). It is recognized that measurements of true reaction temperature under the dynamic conditions present within a reactor are very difficult to measure accurately. However, such temperatures can be estimated, for example, by means of thermocouple in the reaction zone and by observing the resultant temperature profile. The sulfonation process may also be run above or below atmospheric pressures.

As noted above, the invention is adaptable to be used with a wide variety of prior art processes and apparatuses, upon which the invention is a substantial improvement. Thus, a particular reaction vessel may be in a horizontal, vertical or angularly inclined position, and be adapted for continuous, batch, quasi-continuous or cascading operation. Preferably, the reactable mixture is in the form of a falling liquid film, since such falling films appear to have advantages of improved reaction control, better versatility, simplicity of design and large-scale continuous operation as well as other advantages.

A preferred basic sulfonation process is described in the above Knaggs et al U.S. Pat. No. 3,169,142. Briefly, sulfonation is carried out in accordance with that process by inducing marked turbulence in a liquid film containing sulfonatable components with a pressurized stream of an inert diluent and vaporized sulfur trioxide which is impinged onto such a film. The inert diluent is gaseous and may be dry air, "$SO_3$ converter gas" from a sulfur burner catalytic converter which generally comprises a mixture of 5 to 10% $SO_3$ in dry air, nitrogen, carbon dioxide, carbon monoxide, sulfur dioxide, methane, ethane, propane, butane, pentane mixtures thereof or other dry gases. The diluent gas may be passed only once or it may be recycled in the process, as desired.

As the Knaggs et al process is practiced in accordance with the principles of the instant invention, a selected petroleum oil feed stock mixed with an additive is caused to flow along the inner walls of a single tube or preferably a plurality of downwardly inclined reactor tubes in a film form. The film of the oil-additive mixture (which may be preheated) is impinged upon by a dilute vaporized sulfur trioxide reagent at substantial velocities so as to create marked tubulence in the film. The sulfonation reaction itself is extremely fast, with the residence time of the sulfur trioxide inert gas mixture, which is usually directed into contact with the film by means of a suitable gas inlet device, characteristically being less than about 0.5 seconds. The gas temperature in an exemplary embodiment ranges from about 25° to 80° C. (about 77° to 179° F.) at a line pressure ranging from about 2 to 20 psi. The reactor itself may be of a single tube or a plurality of tubes of various diameters and lengths. To effect such a desired rapid reaction and rapid heat exchange, marked turbulence should be produced in the reaction zone, and the Knaggs et al process provides sufficiently rapid reaction times and heat exchange capabilities. The reactor effluent may vary over a broad temperature range, depending at least in part on the heat exchange capabilities of the reactor, the residence time of the materials within the reactor, the amount of sulfonatable components within the materials being sulfonated, etc.

By proceeding in accordance with the principles of the invention, the extent or degree of reaction between oil feed stocks and sulfur trioxide is generally increased on the order of 200% when additives are added to the petroleum oil feed stock prior to sulfonation reactions, as compared to similar reactions where no additive has been added. Under certain conditions, the increase in the extent of reaction is as high as 500% in comparison with prior art sulfonation processes involving no additives.

Water Treatment Details

In proceeding along the principles of the invention, the relatively hot reactor effluent (generally comprised of petroleum-additive sulfonic acid crude reaction mixture) is admixed with a relatively small amount of water, heated or cooled to an optimum temperature range and maintained under these conditions for a relatively brief period of time.

Generally, the amount of water is relatively minor in comparison to the overall reactor effluent and typically ranges from about 0.5% to 20% or more (on a weight basis of the reaction mixture) and preferably comprises about 3 or 5% to about 10%. As will be appreciated, substantially more water may be added, if desired, but such is not required or advisable unless one seeks to directly produce a dilute slug or oil recovery system.

In a preferred continuous embodiment of the invention, the water treatment step is accomplished by withdrawing the reactor effluent from the reactor via a suitable conduit and injecting water into the conduit to admix within the crude reaction product therein as the mixture flows along the conduit. However, this step may, if desired, be performed batchwise or quasi-continuously by collecting the crude reaction products in a suitable container and adding water to the container from the bottom thereof while either allowing excess material to cascade over the upper container walls into, for example, a neutralization container or the like or simply collecting a predetermined amount of crude reaction product within a given container and adding, with admixture, the requisite amount of water (typically based on amounts of reaction mixture produced from the known amount of reaction materials introduced into the reactor).

The water added to the relatively hot petroleum-acid sulfonic acid crude reaction mixture may be at room temperature or may be heated somewhat above room temperature, such as in the range of about 50° to 150° C. and somewhat more preferably to a temperature in the range of about 80° to 100° C. Higher water temperatures may be used if desired, however, pressure may then be required to prevent excessive losses of water vapor and the like and such higher temperatures do not appear to materially aid the resultant water-treated products. Similarly, lower water temperatures may be used if desired, however, heat may then be required to raise the temperature of the crude sulfonic acid-water mixture sufficiently high for the reaction to occur relatively quickly. Addition of water to the crude sulfonation reaction mixture is generally accomplished by an exotherm and a rise in temperature.

The water treatment time period may be relatively brief on the order of about 1 or 2 minutes, although longer periods on the order of about 60 or more minutes may be utilized if desired. Preferably, contact between the crude petroleum-additive sulfonic acid reaction mixture and the added water extends over a period of about 3 or 5 minutes to about 30 minutes. Substantially longer contact periods may be employed if desired, but such are not generally required.

The resultant acidic water-treated sulfonation reaction mixture is relatively stable and homogeneous, even at room temperatures. These acidic water-treated reaction mixtures are less viscous than comparable non-water-treated reaction mixtures and are thus much more handleable for further processing. Typically, the crude sulfonic mixtures, with or without water treatment, may be subjected to neutralization, extraction, deoiling and/or desalting processes in any order desired or convenient. Generally, proper selection of the type and amount of additive and proper control of the reaction conditions in the initial sulfonation process minimizes an excessive presence of unsulfonated feed stocks and/or salts in the crude reactor mixtures and in many instances these further processing steps may be avoided.

Typically, the crude acidic water-treated reaction mixture is first neutralized, and optionally desalted and/or extracted to attain active sulfonate materials useful in various fields, such as in formulating desired micellar systems for use in enhanced oil recovery. Neutralization is conventionally accomplished by the addition of an alkali (such as NaOH, $NH_4OH$, KOH, $NH_3$, etc.) generally as a somewhat diluted aqueous solution, i.e., a 50% NaOH solution. The amount of alkali added is calculated to be sufficient to achieve a pH of about 3 to 12 in the resultant mixture and somewhat preferably to achieve a pH of about 6 to 11.

Products

In general, a product of this invention is a mixture of petroleum oil feed stock and additive, as explained above, which has been sulfonated with sulfur trioxide treated with a small amount of water, neutralized and preferably although not necessarily extracted as expalined above. Such a product comprises a substantially homogeneous and stable material, at least under reaction conditions (and even at room temperatures) and typically is sulfonated to an extent such that at least about 10 weight percent of the sulfonatable components thereof are sulfonated (total product composition weight basis).

In summary, a product of this invention is characterized by:

(A) from about 5 to 98 weight percent of monosulfonated hydrocarbon material;

(B) from about 0 to 50 weight percent of polysulfonated hydrocarbon material; and (C) from about 2 to 90 weight percent of non-sulfonated hydrocarbon material.

Such product composition is prepared by contacting a liquid hydrocarbon mixture with a gaseous sulfur trioxide composition at a suitable temperature, subjecting the resultant crude reaction products so attained to a water-treatment process and neutralizing the so-treated crude products which may then be utilized as such in a desired microemulsion system or may be subjected to extraction to remove salt and/or free oil that may be present within the crude products so-attained, all as described above.

Many of the described additives are also sulfonated or sulfated wholly or partially during the sulfonation reaction between petroleum oil feed stocks and sulfur trioxide. For example, the alcohol additives and the ether alcohol additives are generally sulfated during such reaction, while the alkaryl additives may be sulfonated during the reaction. Such fully or partially sulfonated additive derivatives also function as additives as such, and may be initially added to a petroleum oil feed stock to promote compatibility between petroleum sulfonates and oil under the reaction conditions or may be blended with the ultimately attained reaction products as an aid in forming stable micellar dispersions used in oil recovery processes. Further, these additive derivatives do not detract from the useful characteristics of the ultimate reaction product and may remain therein. In some instances, high additive levels may be preferred to further enhance oil recovery properties, particularly in higher salinity systems, etc. In certain instances, it may be desirable to separately sulfonate select additives and admix such separately sulfonated additives with sulfonated petroleum products (which may or may not include additives therein), or to sulfonate on select portions of an additive molecule, such as on an aromatic portion thereof, to increase the salinity and/or hard water tolerance of the resultant sulfonated petroleum product (which, of course, may comprise a mixture of various specific sulfonated petroleum products).

The water-treated reaction products of the invention are preferably neutralized and may be used as such without further purification (such as desalting, deoiling or phase separation, etc.) and generally comprise a mixture of petroleum sulfonates, unsulfonated petroleum feed stock components, sulfonated and unsulfonated additives, along with various other minor constituents, such as salts. If desired, the sulfonates may be separated and/or the additives recovered for recycling, however, from an economical viewpoint, such further purification or separation of materials may not be justified and from an oil recovery viewpoint such separation of materials is not recommended. Further, when neutralized, the amount of alkali (such as NaOH, $NH_4OH$, KOH, $NH_3$, etc.) may be so controlled that the resultant products have a pH in the range of about 3 to 12 and preferably in the range of 6 to 11.

The reaction products and/or components thereof, such as the petroleum sulfonates have numerous fields of use, for example, as industrial surfactants, as blending agents for lubricating oils, as surface-active agents, as emulsifiers, dispersants, etc. A particularly attractive use for the reaction products of the instant sulfonation process (which include the additives, which themselves may be sulfonated) is in petroleum recovery operations, particularly as surfactants for aiding the recovery of crude oils from so-called depleted fields or wells, for example, as described by G. P. Ahearn in an article in the Journal of American Oil Chemists' Society, October 1969 (Vol. 46), pages 540 A et seq., entitled "Surfactants for Oil Recovery" or in U.S. Pat. No. 3,302,713, both of which are incorporated herein by reference. The petroleum sulfonate products obtained in the practice of the invention are extremely useful in forming so-called dispersion or micellar systems and/or microemulsions or emulsions as well as other systems which are used in enhanced or secondary recovery of petroleum. The petroleum sulfonates obtained in the practice of the invention may be added to or used to replace all or part of various other surface-active agents in various prior art oil recovery systems, such as described, for example, in U.S. Pat. Nos. 3,254,714; 3,297,084; 3,307,628; 3,330,343; 3,348,611; 3,356,138; 3,368,621; 3,408,611; 3,476,184; 3,493,047; 3,493,048; 3,497,006; 3,500,912; 3,504,744; 3,506,070; 3,506,071; 3,653,440; 3,769,209; 3,830,301; 3,873,453; 3,885,626; and 3,885,628 (all of which are incorporated herein by reference), as well as in other somewhat similar systems. In many instances, no further changes in the compositions of such oil recovery systems, whether micellar, dispersion, emulsion or otherwise, will be required. In other instances where larger or smaller amounts of petroleum sulfonates (reaction products) obtained in the practice of the invention are required, workers skilled in the art can readily determine the optimum amount by routine production of a desired system and routine evaluation of such system, for example, with the aid of core-flooding tests or the like.

Further Processing of Products

In further embodiments of the invention, the above described basic petroleum oil sulfonation process may be supplemented by a number of further optional processes. For example, the reaction products (a mixture of petroleum sulfonates, unsulfonated oils, sulfonated and unsulfonated additives, etc.) neutralized to a pH in the range of about 3 to 12 may be subjected to extraction, deoiling and/or desalting processes. Generally, proper selection of the type and amount of additive and control of the reaction conditions in the basic sulfonation process minimizes an excessive presence of unsulfonated oils and/or salts in the reaction products (typically the amount of salts in neutralized products may range from about 0.1 to 10% by weight); and in many instances these further processing steps may be avoided. This constitutes a further advantage of the invention. However, in those instances where such optional steps are desired, they may be performed, for example, by adding water or a mixture of water and an alcohol, such as $C_1$-$C_5$ alcohols or semipolar organic compounds, for example, isopropyl alcohol or benzene to the reaction products to achieve a phase separation and then simply removing the unsulfonated (unsulfonatable and non-sulfonated) oils or raffinate phase, which is substantially insoluble in the hydrophilic solvent. If desired, the unsulfonated oils may be recycled through the sulfonation reaction or may be otherwise disposed of and any alcohol or other valuable component therein recovered for further use. This deoiling process may be followed by or preceded by a desalting process wherein the water-treated acidic reaction products are neutralized to form a desired salt, such as with sodium or ammonium hydroxide and the resultant salt precipitates from the solution and which can then be separated by centrifugation, filtration, etc. (although small amounts of salt may remain in the product without detrimental effect). The deoiling process may also be performed on the neutralized reaction products, if so desired, and since some solvent may carry over with the extracted phase, such phase may be distilled or otherwise purified to recover any solvent therein for further use, or left in, if desired. Separation, such as may occur on cooling of essentially unreacted oils from crude sulfonic acid mixtures may be effected by decantation or other phase separating processes, although the water-treatment step of the invention tends to minimize any such separation.

Additionally, the reaction products may be subjected to a digestion process whereby the reaction products are held or stored in a container for some period of time, such as 20 minutes, while they are maintained at some desired temperature or cooled down from the heat of reaction. In a modified form of the digestion process, the reaction products are maintained at a select temperature and some heat may be applied. Such a digestion process is recommended to react traces of dissolved sulfur trioxide with sulfonatable oil components and/or sulfonatable additive components and to reduce the sulfuric acid content in the reaction products.

The digestion process may be coupled with a number of further steps. For example, additional amounts of additives may be intermixed with the reaction products during digestion or thereafter. Many of the additives described herein tend to further reduce the sulfuric acid content and react with any sulfur trioxide present in the reaction products. The additives added at this stage may be the same or different from those present in the sulfonation reaction zone.

A further optional treatment of the sulfonation reaction products comprises a sequential combination of digestion and heat treatment. Typically, after digestion, the reaction products are heated or held at a temperature ranging from about 35° to 150° C. (95° to 302° F.) for a brief period of time. This combination of steps is designed to further complete the sulfonation reaction and reduce the sulfuric acid content in the ultimate reaction products.

Yet a further optional treatment of the reaction products involves digestion, followed by heat-treatment and further addition of additives to effect a complete reaction as set forth above.

In addition, other conventional steps may be utilized following the initial sulfonation reaction, such as degassing, filtration and/or neutralization. For example, the water-treated sulfonation reaction products, which are acidic in nature, may be first neutralized, such as with an economical material, for example, sodium hydroxide, followed by removal of resultant salt, as by the addition of a suitable solvent and then followed by filtration, centrifugation, etc.

Thus, one has the option of utilizing any combination of the post-sulfonation steps described hereinabove to achieve desired characteristics in the reaction product. Under certain reaction conditions, generally at somewhat higher reaction temperatures, immediate neutralization of the water-treated reaction products is preferable so as to avoid decomposition of reaction products, possible desulfonation or other undesirable reactions.

EMBODIMENTS

With the foregoing general disclosure in mind, a number of detailed examples are presented which will illustrate to those skilled in the art the manner in which this invention is carried out. However, the examples are not to be construed as limiting the scope of the invention in any way and the examples merely point out the efficacy of the invention in attaining the high degree or extent of reaction between sulfonatable components of various oil petroleum feed stocks with gaseous sulfur trioxide in the presence of the additives described hereinabove and demonstrate a preferred utility of the so-attained sulfonated compositions.

DEMONSTRATION I

A series of runs, shown below, were conducted to demonstrate the improved performance of petroleum sulfonates obtained in accordance with the invention against otherwise substantially identical sulfonates which, however, had not been subjected to water treatment as required by the principles of the invention.

A select petroleum feed stock, generally characterized as a paraffinic petroleum oil having the following properties:

| | |
|---|---|
| Average molecular weight | 390 |
| API Gravity (at 60° F.) | 14.3 |
| Pour Point (in °F.) | +70 |
| Boiling Range (in °F.) | 661° to 904° | was admixed with 4% (by weight of feed stock) of an oxo alcohol polymer bottoms (identified as Houdry $C_8$ alcohol bottoms), was then sulfonated via the techniques of Knaggs et al. U.S. Pat. No. 3,169,142 in a laboratory model six-foot reactor tube whereby a liquid film of the above petroleum feed stock-additive mixture flowing within the reactor tube was impinged by a gaseous mixture of nitrogen (or some other inert gas) and sulfur trioxide, containing a ratio of about 95:5 of nitrogen to sulfur trioxide. The gas mixture temperature at the initiation of the sulfonation reaction was maintained at about 35° C. (95° F.) and the pressure of the gas mixture within the reaction zone (i.e., the interior of the reactor tube) was about 3 to 5 psig. The petroleum feed stock-additive mixture was heated to a feed temperature of about 50° to 55° C. (122° to 131° F.). The reactor tube was steam-jacketed and the crude sulfonation product outlet temperature was about 110° C. (230° F.). The liquid film feed rate was set at about 100 gr./min. and the gas velocity into the reactor tube was set at about 95 ft./sec. so that an $SO_3$ feed rate of about 15 to 20 gr./min. was attained.

The crude sulfonic acid so-obtained was then separated into four portions and two portions, designated I-A and I-B, respectively, were treated as follows:

Portion I-A was neutralized with a 50% NaOH solution until a pH of about 10 was attained. The resulting crude sodium petroleum sulfonate was then admixed with isopropanol and water in the ratio of 2:1:1 (all by weight of sulfonate to alcohol to water) and maintained at about 140° F. for one hour. Three layers formed and were separated in a conventional manner. The middle layer, which comprised mainly of sodium petroleum sulfonate, unreacted feed stock, salt, water and isopropanol was heated under vacuum to remove the alcohol and some water. The resulting material was analyzed as comprising about 60% active sodium petroleum sulfonate.

Portion I-B was first mixed with 7.5% water (based on weight of reaction mixture) and maintained at about 85° to 95° C. for about 6 minutes. Thereafter, the so water-treated crude sulfonic acid material was neutralized with 50% NaOH to a pH of about 10, and separated as described above for portion I-A, correcting for the 7.5% water addition. After stripping alcohol and some water, as above, the remaining material was analyzed as comprising about 60% active sodium petroleum sulfonate.

The sodium petroleum sulfonates, designated sample I-A and I-B, respectively, were then identically formulated into microemulsion slugs and tested for oil recovery performance using an Illinois crude oil with a standard Berea sandstone core prepared as follows:

2" × 12" cylindrical Berea sandstone cores were fired at 825° F. for 24 hours, side surfaces thereof encapsuled with an epoxy resin flushed with a standard brine solution (water containing 1.5% NaCl and 100 ppm of $Mg^{++}$ and $Ca^{++}$); saturated with the Illinois crude oil; flushed with the above standard brine solution (secondary recovery) and the residual oil, after brine flushing, was calculated and used to determine the percentage of tertiary or enhanced oil recovery attained by forcing the respective slugs through such cores. Pertinent data is set forth below:

TABLE A

| Sample | Water Treat | Slug Composition | | Co-Surfactant[1] | Residual Oil Recovery | Slug[2,3] P.V. |
|---|---|---|---|---|---|---|
| | | Act. Sulf. | NaCl | | | |
| I-A | No | 3.0% | 1.5% | 0.7% | 29.1% | 0.05 |

TABLE A-continued

| Sample | Water Treat | Slug Composition | | Co-Surfactant[1] | Residual Oil Recovery | Slug[2,3] P.V. |
|---|---|---|---|---|---|---|
| | | Act. Sulf. | NaCl | | | |
| I-C | Yes | 3.0% | 1.5% | 0.65% | 52.7% | 0.05 |

[1]n-Hexanol
[2]Pore Volume
[3]The slug was followed by an aqueous solution of 1500 ppm of Dow-Pusher 700 in 0.5% NaCl.

As can be seen from the above data, petroleum sulfonate treated in accordance with the principles of the invention provide substantially better oil recovery and it will be appreciated that deliberately low slug pore volumes were utilized to accentuate differences, whereas higher pore volumes are more generally utilized under actual field conditions and substantially greater oil recovery is expected (typically 60% to 95% oil recovery).

The above described microemulsion slug compositions were tested for oil recovery performance using an Oklahoma crude oil with the earlier described standard Berea sandstone cores. Pertinent data is set forth below:

TABLE B

| Sample | Water Treat | Slug Composition | | Co-Surfactant[1] | Residual Oil Recovery | Slug P.V.[2,3] |
|---|---|---|---|---|---|---|
| | | Act. Sulf. | NaCl | | | |
| I-A | No | 3.0% | 1.5% | 0.71% | 48.9% | 0.05 |
| I-B | Yes | 3.0% | 1.5% | 0.65% | 64.2% | 0.05 |

[1]n-Hexanol
[2]Pore Volume
[3]The slug was followed by an aqueous solution of 1500 ppm of Dow-Pusher 700 in 0.5% NaCl.

As can be seen from the above data, petroleum sulfonates treated in accordance with the principles of the invention provide substantially better oil recovery with diverse crudes.

A third portion, designated I-C, of the crude sulfonic acid obtained under the sulfonation conditions earlier described was neutralized by admixing therewith a 50% NaOH solution until a pH of about 10 was attained, substantially as described earlier.

A fourth portion, designated I-D, of the crude sulfonic acid obtained by the earlier described sulfonation conditions, was admixed with about 7.5% water (by weight, based on weight of reaction mixture) and maintained at about 80° to 90° C. for about 6 minutes. The so-treated materials were then neutralized with a 50% NaOH solution until a pH of about 10 was attained, substantially as described earlier.

The resulting samples, without phase separation (i.e., crude) were then formulated into microemulsion slug compositions and tested for oil recovery performance using an Illinois crude oil with the earlier described Berea sandstone cores. Pertinent data is set forth below:

TABLE C

| Sample | Water Treat | Slug Composition | | Co-Surfactant[1] | Residual Oil Recovery | Slug P.V.[2,3] |
|---|---|---|---|---|---|---|
| | | Act. Sulf. | NaCl | | | |
| I-C | Yes | 3.0% | 1.5% | 0.51% | 47% | 0.05 |
| I-D | No | 3.0% | 1.5% | 0.54% | 40% | 0.05 |

[1]n-Hexanol
[2]Pore Volume
[3]The slug was followed by an aqueous solution of 1500 ppm of Dow-Pusher 700 in 0.5% NaCl.

As can be seen from the above data, even crude petroleum sulfonates treated in accordance with the principles of the invention provide better oil recovery relative to comparable sulfonates not treated in accordance with the principles of the invention.

DEMONSTRATION II

In another run, a different petroleum oil feed stock, comprising a combination of about 67% by weight of the paraffinic feed stock described in Demonstration I earlier and about 33% by weight of another paraffinic petroleum oil feed stock having the following properties:

| | |
|---|---|
| Average Molecular Weight | 480 |
| API Gravity | 14.8 |
| Pour Point (in °F.) | +60° |
| Boiling Range (in °F.) | 596° to 1009° | was admixed with 4% (by weight of feed stock) of the oxo alcohol polymer bottoms described in Demonstration I above, and sulfonated in the manner described in Demonstration I.

The crude sulfonic acid reaction product so-obtained was separated into two portions, respectively designated II-A and II-B and each portion was then separately treated as follows:

Portion II-A was neutralized with a sufficient amount of a 50% NaOH solution thereto until a pH of about 10 was achieved. The crude sodium petroleum sulfonate was then subjected to phase separation (partial unsulfonated oil extraction and desalting) and stripping of alcohol and some water used for extraction as described earlier. The remaining material was analyzed as containing about 60% active sodium petroleum sulfonate.

Portion II-A was first mixed with about 7.5% by weight water (based on weight of sulfonic acid) and maintained at about 85° to 90° C. for about 6 minutes. Thereafter, the so-water treated crude sulfonic acid material was neutralized with 50% NaOH solution thereto until a pH of about 10 was achieved. Phase separation and stripping were then carried out as described above, leaving about 60% active sodium petroleum sulfonate.

Suitable size samples of the above sulfonates were formulated into substantially identical microemulsion slugs and tested under substantially identical conditions for oil recovery using standard Berea sandstone cores, prepared as described earlier and an Illinois crude oil. Pertinent data is set forth below:

TABLE E

| | Slug Composition | | | | | |
|---|---|---|---|---|---|---|
| Sample | Water Treat | Act. Sulf. | NaCl | Co-Surfactant[1] | Residual Oil Recovery | Slug P.V.[2,3] |
| II-A | Yes | 3.0% | 1.5% | 0.42% | 38% | 0.05 |
| II-B | No | 3.0% | 1.5% | 0.52% | 16% | 0.05 |

[1]n-Hexanol
[2]Pore Volume
[3]The slug was followed by an aqueous solution of 1500 ppm of Dow-Pusher 700 in 0.5% NaCl.

As can be seen from the above data, petroleum sulfonates derived from mixed feed stock and treated in accordance with the principles of the invention provide substantially better oil recovery than non-treated, but otherwise identical material.

DEMONSTRATION III

In another series of runs, the paraffinic petroleum oil feed stock described in Demonstration I above, was sulfonated in the reactor tube as described earlier, using different additives identified below in the amounts specified below (all % are by weight). The so-obtained crude sulfonic acids were each maintained separate from the others and each was subjected to the 7.5% water treatment, neutralization, phase separation and stripping described above. The sodium petroleum sulfonates derived from these runs were then tested for oil recovery performance using standard Berea sandstone cores, prepared as described earlier and an Illinois crude oil. Pertinent data is set forth below:

TABLE F

| | | | Slug Composition | | | | |
|---|---|---|---|---|---|---|---|
| Sample | Additive | Water Treat | Act. Sulf. | NaCl | Co-Surfactant[1] | Residual Oil Recovery | Slug P.V.[2,3] |
| III-A | 4% Oxo Alcohol 4% Octadecene | Yes | 3.0% | 1.5% | 0.78% | 86% | 0.20 |
| III-B | 8% NA[3] | Yes | 3.0% | 1.5% | 0.82% | 89% | 0.20 |

[1]n-Hexanol
[2]Pore Volume
[3]Nonylphenol-alkoxylated material having an equivalent weight of about 2950

As can be seen from the above data, petroleum sulfonates derived from a feed stock-additive mixture containing different amounts of different additives from those utilized in Demonstration I above, provide improved oil recovery.

DEMONSTRATION IV

In another series of runs, portions of a naphthenic petroleum oil feed stock characterized as follows:

| | |
|---|---|
| Average Molecular Weight | 398 |
| Pour Point (in °F.) | +30° |
| Aniline Point (in °F.) | 119° |
| Boiling Range (in °F.) | 723° to 903° | were admixed with the various additives identified below in the amount specified and each portion was then sulfonated substantially as described in Demonstration I. The respective crude sulfonic acids were subjected to the 7.5% water treatment, phase-separation and stripping as described earlier. The respective sodium petroleum sulfonates derived from these runs were then tested for oil recovery performance using standard Berea sandstone cores, prepared as described earlier and an Illinois crude oil. Pertinent data is set forth below:

TABLE G

| Sample | Additive | Water Treat | Slug Composition | | | Residual Oil Recovery | Slug P.V.[2,3] |
| --- | --- | --- | --- | --- | --- | --- | --- |
| | | | Act. Sulf. | NaCl | Co-Surfactant[1] | | |
| IV-A | 4% Octadecyl benzene | Yes | 3.0% | 1.5% | 0.82% | 46% | 0.20 |
| IV-B | 4% $C_8$-$C_{10}$ fatty acid mixture | Yes | 3.0% | 1.5% | 0.90% | 73% | 0.20 |
| IV-C | 4% Octadecene | Yes | 3.0% | 1.5% | 1.10% | 75% | 0.20 |

[1]n-Hexanol
[2]Pore Volume
[3]The slug was followed by an aqueous solution of 1500 ppm of Dow-Pusher 700 in 0.5% NaCl.

As can be seen from the above data, petroleum sulfonates derived from feed stock-additive mixtures containing different feed stock, different amounts of different additives from those utilized in Demonstration I provide improved oil recovery results, although the specific alkaryl additive here utilized was not as effective as the fatty acids or the olefin here utilized for this specific crude oil and oil recovery system.

DEMONSTRATION V

In yet another test, a petroleum oil feed stock having the following characteristics:

| | |
| --- | --- |
| Average Molecular Weight | 390 |
| API Gravity | 14 |
| Viscosity (55 at 210° F.) | 80 |
| Pour Point (in °F.) | 65 | was admixed with 2% (by weight of feed stock) of n-hexanol and 2% (by weight of feed stock) of n-octanol and the resultant liquid mixture was sulfonated in the laboratory reactor tube earlier described under the following operating conditions:

| | |
| --- | --- |
| Liquid feed temp. | 190° F. |
| Liquid feed rate | 99.9 gr/min. |
| Gas velocity | 95 ft./sec. |
| Inert gas/$SO_3$ temp. | 179° F. |
| Reactor jacket temp. | 182° F. |
| Crude product temp. | 213° F. |
| Pressure | 3.5 psi |

The crude reaction product was collected and 7.5% water was injected into such reaction product. The resultant mixture was then maintained at 80° to 85° C. for about 5 minutes, followed by neutralization with 50% NaOH as described earlier. Analysis of the so-derived crude sodium petroleum sulfonate, designated sample V-A was as follows:

| | |
| --- | --- |
| Actives | 28.9% |
| Free Oil | 46.0% |
| Water | 17.9% |
| Salt | 7.3% |
| Equivalent Wt. | 461 |

The above sample V-A was then formulated into a microemulsion slug containing 3% actives therein and was tested for oil recovery performance using an Illinois crude oil with standard Berea sandstone cores, prepared as described earlier. The formulated slug was pressure-injected into a test core, followed by 0.5 P.V.[2] of a polymer pusher, such as a commercially available polymer pusher, under the trade designation "Dow Pusher 700" and 1.0 P.V.[2] of the standard brine solution (water containing 1.5% NaCl and 100 ppm of $Mg^{++}$ and $Ca^{++}$). The pumping rate was controlled so that a frontal velocity of liquid within the core was about 12 inches per 24 hours and pressure traces were obtained using transducers and strip chart recorders operationally coupled to the test core. The pressure applied to the core varied from about 0.76 to 1.7 psig. Pertinent data is set forth below:

TABLE H

| Sample | Water Treat | Slug Composition | | | Residual Oil Recovery | Slug P.V.[2,3] |
| --- | --- | --- | --- | --- | --- | --- |
| | | Act. Sulf. | NaCl | Co-Surfactant[1] | | |
| V-A | Yes | 3% | 1.5% | 0.08% | 60.9% | 0.15 |

[1]n-Hexanol
[2]Pore Volume
[3]The slug was followed by an aqueous solution of 1500 ppm of Dow-Pusher 700 in 0.5% NaCl.

DEMONSTRATION VI

In the miceller slug formulation typically formulated with petroleum sulfonates of the invention. 3.0% of an active petroleum sulfonate is admixed with 1.5% NaCl in water to yield a "cloudy" solution. Hexanol (or some equivalent co-surfactant) is then incrementally added, as with a microliter syrine, to attain a visually "clear" solution. One more drop of hexanol produces a solution sepration into two phases. The volume of hexanol added to produce a clear solution relative to the total slug volume is referred to as the percent of hexanol uptake.

Many workers in the field of enhanced oil recovery via micellar systems use a slug composition formulation near the above-defined clear point as the optimum formulation for maximum oil recovery. Thus, according to presently available information, hexnaol (or some equivalent co-surfactant) uptake is generally related to maximum oil recovery and provides a convenient method of determining the relative efficiency of various petroleum sulfonates.

As will be appreciated, the less hexanol required to reach this optimum point, the more economical is the particular formulation. It was earlier shown that water treatment of petroleum sulfonic acid produced in accordance with the principles of the invention reduces the hexanol uptake of micellar system slug formulations formed from such products and yields improved oil recovery. The instant demonstration shows additional parameters involving the principles of the invention.

In this test, petroleum oil feed stock defined in Demonstration V was admixed with 4% (by weight of feed stock) of an oxo-alcohol polymer bottoms (identified as U.S. Steel $C_{10}$ alcohol bottoms) and the resultant mixture was sulfonated in the laboratory reactor tube earlier described under reaction conditions approximately identical to those utilized earlier.

The crude sulfonic acid so-obtained was collected and a portion thereof was separated into 17 samples, respectively designated VI-A through VI-Z and VI-Control, which were then further treated (i.e., heated with or without the addition of water), neutralized, extracted, formulated into slug compositions and treated with hexanol as described earlier. Pertinent data is set forth below:

TABLE I

| Samples | % Water Added | Temp.(°C.) | Time(Min.) | % Hexanol[1] Uptake |
|---|---|---|---|---|
| VI-A | 0.5 | 150 | 60 | — |
| VI-B | 1.5 | 100 | 30 | 0.32[2] |
| VI-C | 1.5 | 150 | 30 | — |
| VI-D | 3.0 | 100 | 2 | 0.34[2] |
| VI-E | 3.0 | 100 | 6 | 0.30 |
| VI-F | 15.0 | 50 | 2 | 0.42 |
| VI-G | 15.0 | 50 | 30 | 0.37 |
| VI-G' | 15.0 | 50 | 30 | 0.35 |
| VI-H | 20.0 | 50 | 2 | 0.42 |
| VI-I | 20.0 | 50 | 60 | 0.40 |
| VI-V | 7.5 | 92 | 5 | 0.28 |
| VI-W | 7.5 | 95 | 3 | 0.24 |
| VI-X | 7.5 | 94 | 2 | 0.25 |
| VI-Y | 5.0 | 92 | 3 | 0.28 |
| VI-Z | 10.0 | 93 | 3 | 0.25 |
| VI-Control | None | None | None | 0.42 |

[1]Volume % of primary hexanol added to 3.0% Active/1.5% NaCl aqueous micellar solutions to achieve a visually clear point at 25° C.
[2]Evidence of sulfonic acid decomposition reported during the "high temperature" acid treatment.

As can be seen from the above data, the VI-Control sample (no water treatment) slug required 0.42% hexanol to reach the clear point whereas with an identical sulfonic acid provided with an addition of 7.5% water and held at a temperature of 95° C. for 3 minutes (Sample VI-W) only required 0.24% hexanol. The above data exhibits a trend showing that reduced water addition (to 0.5%) and increased reaction temperatures (to 150° C.) results in acid deterioration but does show improvements in hexanol uptake. Similarly, the above data indicated a trend showing that increased water addition and increased reaction time at decreased reaction temperatures (Samples VI-F through VI-I) and/or decreased additions of water and increased reaction times and temperatures (Samples VI-B and VI-C) result in improvements in hexanol uptake (i.e., less hexanol is required) but more optimal results can be obtained when the previously defined preferred water treatment parameters are selected.

DEMONSTRATION VII

In another test for hexanol uptake efficiency, the slug formulation was changed to the following:
10% active sulfonate
30% total hydrocarbon
1% NaCl
59% water and minor amounts of inorganic material.

The above slug formulations were then admixed with incremental amounts of hexanol to the clear point as explained earlier.

In this test, an amount of petroleum sulfonic acid from Demonstration VI was isolated and divided into ten samples, designated VII-Control and VII-1 - VII-9, and each sample was then treated and studied for hexanol uptake as described earlier. Pertinent data is set forth below:

TABLE J

| Sample | Water Addition | Temp.(°C.) | Time(Min.) | % Hexanol Uptake |
|---|---|---|---|---|
| VII-Control | No | | | 0.36% |
| VII-1 | No | 90 | 5 | 0.23 |
| VII-2 | 5% | 90 | 5 | 0.15 |
| VII-3 | 7.5% | 90 | 5 | 0.11 |
| VII-4 | 10.0% | 90 | 5 | 0.15 |
| VII-5 | No | 100 | 5 | 0.34 |
| VII-6 | 5% | 100 | 5 | 0.04 |
| VII-7 | 7.5% | 100 | 5 | 0.03 |
| VII-8 | 10% | 100 | 5 | 0.15 |
| VII-9 | No | 120 | 5 | 0.26 |

As can be seen from the above uptake data, a definite reduction in the amount of hexanol uptake occurs with water-treated samples whereas non-water treated but digested samples (samples heated to reaction temperatures for an identical period of time as the water-treated samples) show an erratic hexanol uptake.

DEMONSTRATION VII

In order to study the relationship of water treatment relative to the mode of neutralization, an amount of the crude petroleum sulfonic acid from Demonstration VI was isolated and divided into three samples, designated Samples VIII-A, VIII-B and VIII-C, which were then treated as follows:
Sample VIII-A—7.5% of H$_2$O added, heated at 95° C. for 5 minutes and then neutralized with 50% NaOH to a pH of about 10.
Sample VIII-B—Non-water treated sulfonic acid added to 50% NaOH until a pH of about 10 was achieved.
Sample VIII-C—50% NaOH added to non-water treated sulfonic acid until a pH of about 10 was achieved.

The resulting products were then analyzed and pertinent data is set forth below:

TABLE K

| Sample | Equivalent Weight | % Hexanol Uptake |
|---|---|---|
| VIII-A | 419 | 0.16 |
| VIII-B | 401 | 0.53 |
| VIII-C | 410 | 0.24 |

As can be seen from the above data, the lowest hexanol uptake is achieved with the water-treated sample. Another indication of an improved sulfonate product is the higher EW for the water-treated sample. The above data also indicates that under these conditions it is preferable to add a base to an acid rather than vice versa.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting in the present invention, excepting as it is set forth and defined in the hereto-appended claims.

We claim as our invention:
1. A method for preparing petroleum sulfonates comprising the sequential steps of
(I) intimately contacting from about 5 to 40 parts by weight of sulfur trioxide with 100 parts by weight of a flowable liquid mixture, which comprises on a 100 weight percent total mixture basis:

(A) from about 85 to 99.5 weight percent of a petroleum oil feed stock, and (B) from about 0.5 to 15 weight percent of an additive, said petroleum oil feed stock being characterized by (a$_1$) having an API gravity ranging from about 5° to 60° at 60° F., (a$_2$) having a boiling point (corrected atmospheric) ranging from about −20° to 1400° F., and (a$_3$) containing from about 10 to 95 weight percent (100 weight percent total stock basis) of sulfonatable components, said additive being characterized by (b$_1$) being comprised of unsulfonatable organic radical portions possessing an average molecular weight range from about 55 to 6000, (b$_2$) having a boiling point in the range from about 212° to 932° F. corrected atmospheric, and (b$_3$) a preponderance of such radicals each having attached at least one proton replaceable by a sulfo group and at least one moiety selected from the group consisting of an aromatic nucleus, an olefinic carbon pair, and an oxygen atom directly bonded to a carbon atom by at least one bond, said contacting being conducted at a temperature of from about 77° to 392° F., said contacting being continued for a time at least sufficient to sulfonate at least about 10 weight percent of the total sulfonatable components present in said petroleum oil feed stock so as to attain a crude acidic sulfonation reaction mixture; and (II) intimately contacting said crude acidic reaction mixture with about 0.5% to about 20% by weight, on a 100 weight percent total reaction mixture basis, of water and maintaining the so-attained mixture at a temperature of about 50° to about 150° C. for a period of time ranging from about one minute to about 60 minutes.

2. A method as defined in claim 1 wherein the amount of water brought into intimate contact with the crude acidic reaction mixture is about 2% to about 10% by weight, on a 100 weight percent total reaction mixture basis.

3. A method as defined in claim 1 wherein the crude acidic reaction mixture-water mixture is maintained at a temperature of about 80° to about 100° C.

4. A method as defined in claim 1 wherein the crude acidic reaction mixture-water mixture is maintained at said temperature for a period of time ranging from about 2 to about 30 minutes.

5. A method as defined in claim 1 including intimately contacting the crude acidic reaction mixture-water mixture attained after step II with a sufficient amount of a base to attain a pH within the resultant mixture in the range of about 3 to 12.

6. A method as defined in claim 5 wherein the amount of base brought into intimate contact with said crude acidic reaction mixture-water mixture is sufficient to attain a pH within the resultant mixture in the range of about 6 to 11.

7. A method as defined in claim 5 including extracting the base-treated crude acidic reaction mixture-water mixture so as to remove salts and free oil.

8. A method as defined in claim 1 wherein said flowable liquid comprises a film and a continuous reaction takes place.

9. A method as defined in claim 1 wherein said flowable liquid is confined within a reaction vessel and a batch reaction takes place.

10. A method as defined in claim 1 wherein said flowable liquid is confined within a reaction vessel and a continuous adding of reactants, and continuous removal of reaction products takes place to effect a quasi-continuous sulfonation.

11. A method as defined in claim 1 wherein said petroleum oil feed stock includes aromatic portions which have a molecular weight in the range of about 200 through about 1000.

12. The method of claim 1 wherein said contacting is continuously accomplished by the steps of forming a flowing liquid film of said mixture on a temperature-controlled reaction surface;

impinging said liquid film with a mixture of gaseous sulfur trioxide and an inert gas so as to attain a sulfonation reaction between sulfonatable components in said film and sulfur trixode;

controlling the reaction temperature so as to maintain said reaction temperature in the range of about 77° to about 392° F., and injecting about 2% to about 10% water into the so-attained reaction mixture while maintaining the temperature of the resultant mixture in the range of about 50° to 150° C. for a period of time ranging from about 2 to about 30 minutes.

13. A method as defined in claim 12 wherein said additive includes at least one $C_2$ to $C_{30}$ main hydrocarbon chain and is characterized as having a boiling point in the range of about 212° to 932° F.

14. A method as defined in claim 13 wherein said additive is selected from the group consisting of unsaturated aliphatic hydrocarbon compounds, substituted and unsubstituted aromatic compounds, olefinic compounds, oxygen-containing compounds, hydroxy-containing compounds, ester compounds, ether compounds, ester-ether compounds, ketone compounds, fatty acid compounds and mixtures thereof.

15. A method as defined in claim 12 wherein said additive is a $C_4$ to $C_{28}$ oxygen-containing compound characterized as having a boiling point in the range of about 212° to 932° F.

16. A method as defined in claim 15 wherein said oxygen-containing compound is a hydroxy-containing compound.

17. A method as defined in claim 16 wherein said hydroxy-containing compound is a $C_6$ to $C_{28}$ alcohol.

18. A method as defined in claim 17 wherein said alcohol is selected from the group consisting of hexanol, octanol, nonanol, decanol, octadecanol, dodecanol, lauryl, myristyl, palmityl, stearyl and mixtures thereof.

19. A method as defined in claim 15 wherein said oxygen-containing compound is an oxo alcohol still bottom.

20. A method as defined in claim 19 wherein said oxo alcohol still bottom is comprised of about 2 to 20% by weight of octyl alcohol; about 4 to 40% by weight of nonyl alcohol, about 25 to 90% by weight of decyl and higher boiling materials and about 20 to 80% by weight of esters.

21. A method as defined in claim 19 wherein said oxo alcohol still bottom is comprised of about 5% by weight of octyl alcohol, about 10% by weight of nonyl alcohol, about 35% by weight of decyl and higher boiling materials, about 45% by weight of esters and about 5% by weight of soaps.

22. A method as defined in claim 15 wherein said oxygen-containing compound is a phenolic compound.

23. A method as defined in claim 22 wherein said phenolic compound is selected from the group consisting of phenol, $C_1$ to $C_{16}$ alkyl phenols, $C_1$ to $C_{16}$ alkyl $C_1$ to $C_{200}$ alkoxy phenols and mixtures thereof.

24. A method as defined in claim 15 wherein said oxygen-containing compound is a glycol compound.

25. A method as defined in claim 15 wherein said oxygen-containing compound is alkoxylated with about 1 to 200 mols of a $C_2$ to $C_4$ alkylene oxide per mole of oxygen-containing compound.

26. A method as defined in claim 15 wherein said oxygen-containing compound is a tallow alcohol.

27. A method as defined in claim 12 wherein said additive is a $C_4$ to $C_{40}$ olefinic hydrocarbon characterized as having a boiling point in the range of about 212° to 932° F.

28. A method as defined in claim 12 wherein said additive is a $C_6$ to $C_{40}$ aromatic.

29. A method as defined in claim 12 wherein said additive is a $C_4$ to $C_6$ ether characterized as having a boiling point in the range of about 212° to 932° F.

30. A method as defined in claim 29 wherein said ether is selected from the group consisting of 4-methoxy butanol, 2-ethoxy ethanol, 2-propoxy ethanol, 2-butoxy ethanol, diethylene glycol, diethylene glycol monoethyl ether, diethylene glycol butyl ether and mixtures thereof.

31. A method as defined in claim 12 wherein said additive is a $C_4$ to $C_6$ hydrocarbon ether ester characterized as having a boiling point in the range of about 212° to 932° F.

32. A method as defined in claim 31 wherein said ether ester is selected from the group consisting of acetate ester of diethylene glycol monoethyl ether, acetate ester of ethylene glycol monoethyl ether, acetate ester of butylene glycol monoethyl ether and mixtures thereof.

33. A method as defined in claim 12 wherein said additive is a $C_7$ to $C_{30}$ alkaryl compound characterized as having a boiling point in the range of about 212° to 932° F.

34. A method as defined in claim 12 wherein said additive is a $C_1$ to $C_4$ alkyl ester of a $C_6$ to $C_{20}$ aliphatic acid characterized as having a boiling point in the range of about 212° to 932° F.

35. A method as defined in claim 34 wherein said alkyl ester acid is a methyl ester of a $C_{12}$ to $C_{18}$ fatty acid.

36. A method as defined in claim 34 wherein said alkyl ester acid is a methyl ester of a $C_8$ to $C_{10}$ fatty acid.

37. A method as defined in claim 34 wherein said alkyl ester acid is a methyl ester of a $C_{14}$ to $C_{28}$ fatty acid.

38. A method as defined in claim 12 wherein said additive is a $C_6$ to $C_{28}$ alkyl ester of a $C_6$ to $C_{28}$ aliphatic alcohol characterized as having a boiling point in the range of about 212° to 932° F.

39. A method as defined in claim 12 wherein said petroleum oil feed stock is selected from the group consisting of crude oil, topped crude oil and mixtures thereof.

40. A method as defined in claim 1 wherein said amount of the additive in said mixture ranges from about 0.5% to about 5% by weight of said petroleum oil feed stocks.

41. A method as defined in claim 1 wherein said amount of additive in said mixture ranges from about 2% to about 10% by weight of said petroleum oil feed stocks.

42. A method of claim 1 wherein said contacting is continuously accomplished by the steps of
forming a flowing liquid film of said mixture on a temperature controlled reaction surface, said additive being selected from the group consisting of oxo alcohol still bottoms, $C_4$ to $C_{28}$ aliphatic alcohols, alkoxylated phenols, diethylene glycol monoethyl ether, alkoxylated nonyl phenols, alkoxylated tallow alcohol, 2-butoxy ethanol, acetate ester of diethylene glycol monoethyl ether, $C_8$–$C_{10}$ alcohols, $C_8$–$C_{10}$ fatty acid methyl esters, isopropyl palmitate, hydrogenated $C_{12}$–$C_{16}$ fatty acid methyl esters, acetate ester of ethylene glycol monobutyl ether, $C_8$ to $C_{10}$ fatty acids, branched chain $C_{15}$ alkyl benzene, branched chain dodecylbenzenes, palmitic acid, $C_{14}$–$C_{18}$ α-olefins, mesityl oxide, acetate ester of ethylene glycol monoethyl ether, and mixtures thereof;
impinging said liquid film with a mixture of gaseous sulfur trioxide and an inert gas so as to attain a sulfonation reaction between sulfonatable components in said film and sulfur trioxide;
controlling the reaction temperature so as to maintain said reaction temperature in the range of about 77° to about 392° F.; and
injecting about 2% to about 10% water into the so-attained reaction mixture while maintaining the temperature of the resultant mixture in the range of about 50° to 150° C. for a period of time ranging from about 2 to about 30 minutes.

43. A process of producing, as defined in claim 1, petroleum sulfonates having an average equivalent weight of from about 350 to 550 and being suitable for use in subterranean oil recovery processes, said contacting being accomplished by the steps comprising:
forming a flowable liquid of said mixture on a temperature controlled reaction surface;
contacting said liquid with a gaseous sulfur trioxide so as to attain a sulfonation reaction between sulfonatable components in said liquid and sulfur trioxide;
controlling the reaction temperature so as to maintain said reaction temperature in the range of about 77° F. to about 392° F.; and
(II) intimately contacting said crude acidic reaction mixture with about 0.5% to about 20% by weight, on a 100 weight percent total reaction mixture basis, and maintaining the so-attained mixture at a temperature of about 50° to about 150° C. for a period of time ranging from about one minute to about 60 minutes.

44. The process of claim 1 wherein said contacting is continued for a time at least sufficient to produce a sulfonated composition which comprises on a 100 organic weight percent total weight basis
(A) from about 5 to 98 weight percent of monosulfonated hydrocarbon,
(B) from about 0 to 50 weight percent of polysulfonated hydrocarbon, and
(C) from about 2 to 90 weight percent of non-sulfonated petroleum.

45. A sulfonation product produced by the method of claim 1.

46. A sulfonation product produced by the method of claim 12.

47. A sulfonation product produced by the method of claim 42.

48. A method as defined in claim 1 including intimately contacting the crude acidic reaction mixture-water mixture attained after step II with a sufficient amount of a base to attain a pH within the resultant mixture in the range of about 3 to 12 and subjecting said resultant mixture to an extraction process so as to remove salts and free oil from said resultant mixture.

49. A method as defined in claim 48 wherein said extraction process comprises admixing a hydrophilic solvent selected from the group consisting of water, a $C_1$–$C_5$ alcohol, benzene and mixtures thereof with said base-treated resultant mixture.

50. A sulfonation product produced by the method of claim 2, 3, 4, 5, 6, 7, 8, 9, 10, 11, 13, 14, 15, 16, 17, 18, 19, 20, 21, 22, 23, 24, 25, 26, 27, 28, 29, 30, 31, 32, 33, 34, 35, 36, 37, 38, 39, 40, 41, 43 or 44.

* * * * *